(12) United States Patent
Carrison

(10) Patent No.: US 6,576,000 B2
(45) Date of Patent: Jun. 10, 2003

(54) DEVICES AND METHODS FOR TISSUE REPAIR

(75) Inventor: Harold F. Carrison, Pleasanton, CA (US)

(73) Assignee: SciMed Life Systems, Inc., Maple Grove, MN (US)

( * ) Notice: Subject to any disclaimer, the term of this patent is extended or adjusted under 35 U.S.C. 154(b) by 0 days.

(21) Appl. No.: 09/800,155

(22) Filed: Mar. 6, 2001

(65) Prior Publication Data

US 2002/0128697 A1 Sep. 12, 2002

(51) Int. Cl.[7] .................................................. A61N 1/00
(52) U.S. Cl. ......................................................... 607/92
(58) Field of Search ............................. 607/1, 2, 50, 88, 607/93, 94, 92, 115, 116

(56) References Cited

U.S. PATENT DOCUMENTS

| | | | |
|---|---|---|---|
| 4,636,346 A | 1/1987 | Gold et al. | |
| 4,739,768 A | 4/1988 | Engelson | |
| 4,840,622 A | 6/1989 | Hardy | |
| 4,863,442 A | 9/1989 | DeMello et al. | |
| 5,078,702 A | 1/1992 | Pomeranz | |
| 5,104,392 A | 4/1992 | Kittrell et al. | |
| 5,188,632 A | * 2/1993 | Goldenberg | 385/142 |
| 5,248,312 A | * 9/1993 | Langberg | 606/27 |
| 5,254,112 A | 10/1993 | Sinofsky et al. | |
| 5,445,608 A | * 8/1995 | Chen et al. | 604/19 |
| 5,573,531 A | 11/1996 | Gregory | |
| 5,603,697 A | * 2/1997 | Grundy et al. | 604/95.04 |
| 5,797,869 A | 8/1998 | Martin et al. | |
| 5,833,595 A | * 11/1998 | Lin | 128/DIG. 25 |
| 5,860,948 A | 1/1999 | Buscemi | |
| 5,951,881 A | * 9/1999 | Rogers et al. | 216/41 |
| 6,090,099 A | 7/2000 | Samson et al. | |
| 6,159,187 A | 12/2000 | Park et al. | |
| 6,165,163 A | 12/2000 | Chien et al. | |
| 6,263,249 B1 | * 7/2001 | Stewart et al. | 607/116 |
| 6,287,302 B1 | * 9/2001 | Berube | 606/33 |

* cited by examiner

Primary Examiner—Harold Joyce
Assistant Examiner—Derek Boles
(74) Attorney, Agent, or Firm—Robins & Pasternak LLP

(57) ABSTRACT

Disclosed herein catheters, assemblies comprising a single-lumen catheter having one or more sources of electromagnetic radiation disposed within the wall of said catheter. Methods of using these catheters and assemblies are also provided.

20 Claims, 1 Drawing Sheet

DEVICES AND METHODS FOR TISSUE REPAIR

FIELD OF THE INVENTION

Figure 1:
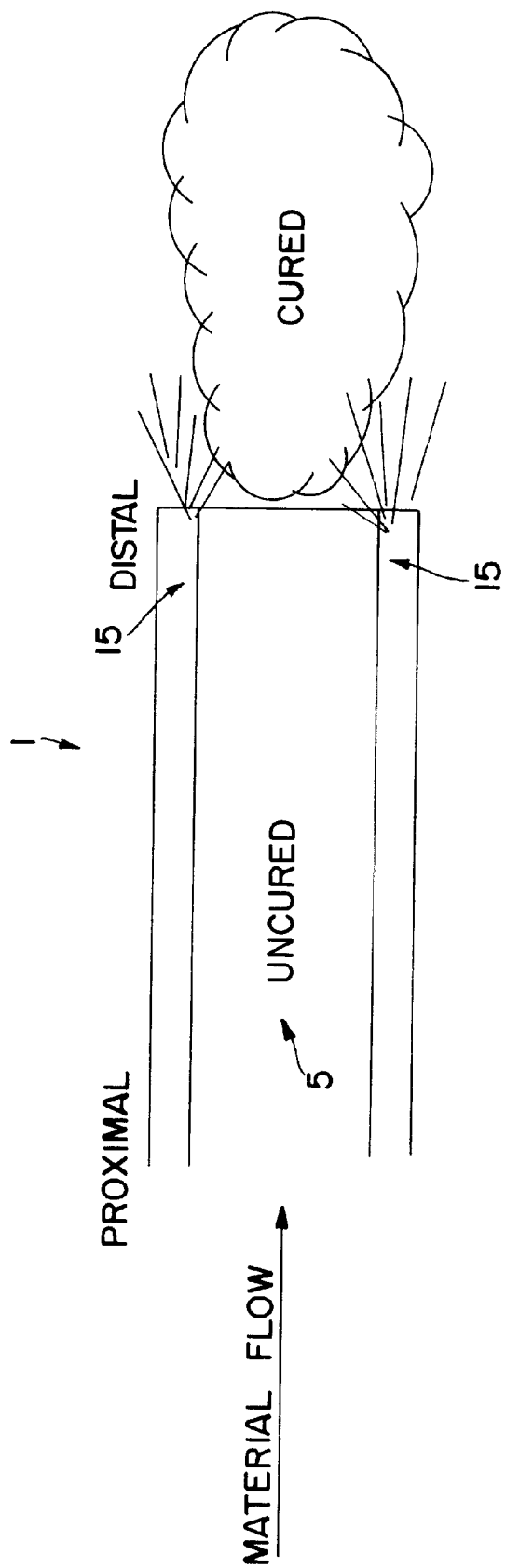

Devices and methods for tissue repair are described. In particular, catheters that can transmit electro-magnetic radiation (e.g., ultraviolet light) to the distal end are described. Also described are methods of using these catheters.

BACKGROUND

Catheters are increasingly used to access remote regions of the human body and, in doing so, delivering diagnostic or therapeutic agents to those sites. In particular, catheters which use the circulatory system as the pathway to these treatment sites are especially useful. For instance, it is commonplace to treat diseases of the circulatory system via angioplasty (PTA) using catheters having balloons on their distal tips. It is similarly common that those catheters are used to deliver a radio-opaque agent to that site prior to the PTA procedure to allow viewing of the problem prior to treatment. Furthermore, vaso-occlusive devices are also delivered through these catheters, for example vaso-occlusive devices such as those found in U.S. Pat. No. 4,994,069, to Ritchart et al, (vaso-occlusive coils); U.S. Pat. No. 5,122,136, to Guglielmi et al (electrolytically detachable vaso-occlusive coils); U.S. Pat. Nos. 5,226,911 and 5,304,194, to Chee et al (vaso-occlusive coils with attached fibers); U.S. Pat. No. 5,250,071, to Palermo (mechanically detachable coils); U.S. Pat. No. 5,261,916, to Engelson (mechanically detachable coil); U.S. Pat. No. 5,304,195, to Twyford et al (mechanically detachable coils); and U.S. Pat. No. 5,312,415, to Palermo (mechanically detachable coils); the entirety of which are incorporated by reference. These devices each have a relatively rigid diameter and must be pushed through the lumen of the delivery catheter.

Catheters for the delivery of these and other materials have been described, for example, in U.S. Pat. Nos. 4,739,768; 6,165,163; 6,159,187 and 6,090,099. Most of these catheters are designed to be used with a guidewire. A guidewire is simply a wire, typically of very sophisticated design, which is the "scout" for the catheter. The catheter fits over and slides along the guidewire as it passes through the vasculature. In other words, the guidewire is used to select the proper path through the vasculature with the urging of the attending physician and the catheter slides along the guidewire once the proper path is established.

Because it is often desirable to use catheters to deliver multiple components to a target site, multi-lumen catheters have also been described. For example, for sealing aneurysms, multi-part materials including vaso-occlusive coils, two-part systems (e.g., adhesive systems such as fibrin based glues), UV curable materials and the like require multi-lumen catheters for delivery of these components. In addition, many of the catheters designed to deliver multi-component systems also require at least one mixing chamber, for example for mixing fibrin glue materials in situ. Multi-lumen catheters are described, for example, in U.S. Pat. No. 5,797,869 to Martin et al.; U.S. Pat. No. 4,636,346, to Gold et al.; U.S. Pat. No. 4,840,622, to Hardy; U.S. Pat. No. 4,863,442, to DeMello et al.; and U.S. Pat. No. 5,078,702, to Pomeranz.

Catheters providing an optical fiber arranged for the transmission and emission of radiation such as UV have also been described. U.S. Pat. No. 5,860,948 describes a catheter comprising a two-lumen catheter apparatus, wherein one of the lumens is in communication with a fluid inlet port and an optical fiber.

However, none of these devices or documents describe catheters having the construction described herein. In particular, none describe a single lumen catheter used for both guidewire and for the placement of soft, photocurable material.

SUMMARY OF THE INVENTION

Thus, this invention includes novel devices as well as methods of using and making these devices.

In one aspect, the invention includes a single-lumen catheter comprising at least one source of electro-magnetic radiation (e.g., ultraviolet light) disposed in the wall of the catheter. In certain embodiments, the source of electro-magnetic radiation is integral to the catheter, for example at the distal end of the catheter. In other embodiments, the source of electro-magnetic radiation comprises a transmission device within the wall of the catheter. The transmission device can then be operably linked to a source of electro-magnetic radiation that is external to the catheter. The electro-magnetic radiation transmission may comprise one or more fiber optic cables; one or more light-transmitting fluids; one or more light-transmitting wires or combinations thereof. Furthermore, the invention can include multiple sources of electro-magnetic radiation (e.g., integral or external source with integral transmission devices) disposed in the wall of the catheter, for example, adjacent to each other or on one or more different sides of the catheter body.

In preferred embodiments, any of the devices and assemblies described herein are used in combination with a source of photopolymerizable material such as polyethyleneglycol diacrylate; poly(ethylene glycol) central block molecules, extended with hydrolyzable oligomers (e.g., oligo(d,l-lactic acid) and oligo(glycolic acid)) and terminated with acrylate groups; and polyethylene glycol tetraacrylate (e.g., initiated with triethanolamine, N-vinylpyrollidone, and/or eosin Y). Photopolymerizable material is preferably suitable for deposition at the target site and wherein electro-magnetic radiation emitted from the source of electro-magnetic radiation disposed in the wall of the catheter polymerizes the photopolymerizable material as it is extruded from the catheter.

In another aspect, the invention includes an assembly for use in depositing material in a vessel comprising any one of the devices described herein; a photopolymerizable material; and a source of electro-magnetic radiation (e.g., ultraviolet light). Thus, in certain embodiments, the source of electro-magnetic radiation is disposed within the wall of the catheter at the distal end of the assembly while in other embodiments, the source of electro-magnetic radiation comprises at least one electro-magnetic radiation transmission device (e.g., one or more fiber optic cable; one or more light-transmitting fluids; and/or one or more light-transmitting wires) disposed within the wall of the catheter and operably linked to an external source of electro-magnetic radiation.

In other embodiments, any of the assemblies described herein further comprise one or more additional bioactive material(s) and/or one or more implantable devices (e.g., vaso-occlusive devices, stents, filters, etc.).

In another aspect, the invention includes a method of occluding an aneurysm comprising administering, to a subject in need thereof, a photopolymerizable material using any of the catheters or assemblies described herein.

DESCRIPTION OF THE INVENTION

This invention involves a single-lumen catheter having one or more means for transmitting electro-magnetic radiation in the wall of the catheter. Thus, the single-lumen of the catheter can be used to deliver a wide variety of embolics and other materials, including but not limited to, photopolymerizable materials (which may be polymerized as they are extruded from the catheter); mechanical devices (e.g. vaso-occlusive devices, stents, filters, etc.); bioactive materials (such as cytokines, growth factors, etc.) or combinations of these materials. As used herein the term "polymerize" or "cure" refers to any forms of cross-linking, chain extension or the like. Thus, "photopolymerizable" refers to any material that can be cross-linked, extended or cured upon the addition of electro-magnetic radiation.

The single-lumen catheters described herein may include one or more sections of varying flexibility and/or composition. Flexible catheters are described, for example, in U.S. Pat. Nos. 6,165,163; 6,159,187; 6,090,099; and 4,739,768 (the entireties of which are incorporated by reference) and each is particularly suitable for neurological and peripheral vascular applications. Clearly, then, the catheters described herein are also suitable for less demanding service such as might be encountered in access and treatment of the heart.

Additional bioactive materials may also be used with these catheters and cure material. The catheters described herein find use in a wide variety of vascular and neurovascular indications and are particularly useful in treating aneurysms. Methods of making and using these devices also an aspects of this invention.

Advantages of the present invention include, but are not limited to, (i) providing the capability of delivering photopolymerizable material in situ using a single-lumen catheter; (ii) providing the ability to polymerize (cure) materials as they are extruded from the delivery catheter; (iii) eliminating the need for mixing chambers required in many multi-part cure systems; (iv) allowing for the delivery of mechanical devices and/or other bioactive material(s) in addition to delivery curable material; and (v) providing a catheter suitable for use in tortuous vessels that can delivery multiple components (e.g., components of curable system; mechanical devices; guidewires; bioactive materials) through a single lumen.

All publications, patents and patent applications cited herein, whether above or below, are hereby incorporated by reference in their entirety.

It must be noted that, as used in this specification and the appended claims, the singular forms "a", "an", and "the" include plural referents unless the content clearly dictates otherwise. Thus, for example, reference to "a photopolymerizable material" includes a mixture of two or more such materials and the like.

FIG. 1 shows one embodiment of a catheter 1 according to the present invention. Shown is a catheter 1 with a single lumen 5. The lumen 5 is capable of accepting, carrying and extruding polymerizable material (e.g., photocurable material); devices (e.g., vaso-occlusive coils, retaining devices, filters, etc.); and/or other bioactive materials. At least one electro-magnetic transmission means (e.g., fiber optic cable, light-transmitting fluid, etc.) 15 is disposed with the wall of the catheter along its outer periphery. Preferably, two transmission means 15 are positioned on opposite side walls of the catheter, although it will be apparent that more than two can also be used and that they can be disposed in any relation to each other within the catheter wall. Furthermore, although not depicted in the Figures, because the transmission devices are positioned in the wall of the catheter, they are therefore separated from the lumen 5 of the catheter by a physical barrier material, preferably the material out of which the catheter is constructed. The distal end 10 of the catheter is configured so that the electro-magnetic radiation transmitted by the electro-magnetic radiation transmission device(s) is emitted just past the distal end of the catheter. In this way, the photocurable material is cured just after extrusion from the catheter. This configuration eliminates the mixing required in many two-part cure systems.

Typical dimensions of the catheter are: overall length 60 to 200 cm; average outside diameter between about 1.0 to 5.0 French (0.013 to 0.65 inches); average inside diameter between about 0.008 to about 0.42 inches. Obviously, these dimensions are not particularly critical to this invention and are selected variously as a function of the malady treated and its site within the body. The catheters may be coated or otherwise treated both inside and outside to increase their lubricity. Such treatments may include silicone oils or, more preferably, hydrophilic polymers.

Any suitable photopolymerizable material can be used, so long as it is not harmful when implanted in the subject. Preferably, the material polymerizes (cures) upon the application of electro-magnetic radiation, preferably UV energy. Non-limiting examples of photopolymerizable materials include, polyethyleneglycol diacrylate or other molecules with a poly(ethylene glycol) central block, extended with hydrolyzable oligomers such as oligo(d,l-lactic acid) or oligo(glycolic acid) and terminated with acrylate groups. Photopolymerizable, biocompatible water-soluble polymers include polyethylene glycol tetraacrylate (Ms 18,500) which can be photopolymerized with an argon laser under biologically compatible conditions using an initiator such as triethanolamine, N-vinylpyrollidone, and eosin Y. Such materials can also be readily designed and manufactured such that they preferentially absorb and polymerize upon application of electro-magnetic radiation (e.g., light). Other suitable materials are described, for example, in U.S. Pat. No. 5,860,948, which is incorporated by reference in its entirety herein. One or more of materials can also be used in various combinations.

The photopolymerizable material is preferably dispersed in a fluid for transport through the lumen of the catheter. Any fluid that is not harmful to the subject may be used. In preferred embodiments, the fluid should be selected so as not to interfere with the transmission of the electro-magnetic radiation and the ability of the electro-magnetic radiation to cure the material(s) upon extrusion from the catheter. For example in the case of UV radiation, saline solution is appropriate.

Thus, any material that is cured by application of electro-magnetic radiation (e.g., light) is suitable for use in the present invention, so long as the amounts and duration of exposure to the energy source is not detrimental to the subject. The visible light spectrum extends from the low-energy red at approximately 7000 Å to the high-energy violet at approximately 4000 Å. Further, non-visible light wavelengths may also be used, for example, gamma rays; ultra-violet light (ranging from about 4000 Å to about 600 Å in wavelength and about 10 eV in energy); infra-red (ranging from about 7000 Å to 1 mm in wavelength and $10^{-3}$ eV to about 1 eV in energy); microwaves (ranging from about 1 mm to 3 cm in wavelength and from about $10^{-5}$ eV to 0.001 eV in energy); ultrahigh frequence (UHF, ranging from about $10^{-7}$ eV to $10^{-5}$ eV in energy) and radio waves (ranging from about $10^{-12}$ eV to about $10^{-8}$ eV in energy).

One or more means for transmitting and/or emitting electro-magnetic radiation are positioned in the catheter, preferably in the wall of the catheter. Thus, the source(s) of electro-magnetic radiation can be external to the catheter or, alternatively, can be built into the catheter. In either case, it is desirable for the source of electro--magnetic radiation be easily controlled (e.g., on-off, type of electro-magnetic radiation, amount, etc.) by the operator. Any source of electro-magnetic radiation can be used to polymerize the photopholymerizable material. Non-limiting examples of sources of electro-magnetic radiation include lasers (e.g., argon lasers) and the like. In certain preferred embodiments, the external source of energy emits UV light, for example in the range of 200-350 nm wavelengths.

Therefore, as noted above, in certain embodiments, the catheter comprises a means for transmitting electro-magnetic radiation to the distal end of the catheter. Non-limiting examples of electro-magnetic radiation transmitting devices include fiber optic cables, light-transmitting fluids, wires, and the like. Other suitable transmitting means or devices will be known to those of skill in the field. In certain embodiments, all of the transmission means in the catheter are the same, for example, one or more fiber optic cables. In other embodiments, a combination of different electro-magnetic transmission devices or means are used. Further, as will be readily apparent, when the source of electro-magnetic radiation is external to the catheter, it is operably linked to the catheter such that the energy can be transmitted down the length of the catheter.

In yet other embodiments, the source of electro-magnetic radiation is itself disposed within the catheter, for example, a laser or other electro-magnetic radiation is disposed at the distal end of the catheter. In these embodiments, it is preferably that the operator maintain the ability to control the emission and/or amount of electro-magnetic radiation emitted from the source. This can be accomplished, for example, by operably linking the source of electro-magnetic radiation to a control mechanism (e.g., power source) that is external to the catheter assembly yet accessible to the operator so that the operator can control the output.

The photopolymerizable materials can be used alone or in combination with one or more implantable devices (e.g., vaso-occlusive devices, stents, filters, etc.), one or more additional bioactive materials or a combination of implantable devices and additional bioactive materials. Suitable implantable devices are known to those skilled in the art. The term "bioactive" refers to any agent which exhibits effects in vivo, for example a thrombotic agent, a therapeutic agent or the like. Non-limiting examples of bioactive materials include cytokines; trace metals (e.g., copper); molecules that stabilize thrombus formation or inhibit clot lysis (e.g., proteins or functional fragments of proteins, including but not limited to Factor XIII, $\alpha_2$-antiplasmin, plasminogen activator inhibitor-1 (PAI-1)); antibiotics; DMSO; or the like. Non-limiting examples of cytokines which may be used alone or in combination in the practice of the present invention include, basic fibroblast growth factor (bFGF), platelet derived growth factor (PDGF), vascular endothelial growth factor (VEGF), transforming growth factor beta (TGF-$\beta$) and the like. Cytokines are commercially available from several vendors such as, for example, Genzyme (Framingham, Mass.), Genentech (South San Francisco, Calif.), Amgen (Thousand Oaks, Calif.), R&D Systems and Immunex (Seattle, Wash.). Additionally, bioactive polypeptides can be synthesized recombinantly as the sequence of many of these molecules are also available, for example, from the GenBank database. It is intended, although not always explicitly stated, that molecules having similar biological activity as wild-type or purified cytokines and thrombus-stabilizing proteins (e.g., recombinantly produced or mutants thereof) and nucleic acid encoding these molecules are intended to be used within the spirit and scope of the invention. Further, the amount and concentration of bioactive materials useful in the practice of the invention can be readily determined by a skilled operator and it will be understood that any combination of materials, concentration or dosage can be used, so long as it is not harmful to the subject.

Conventional catheter insertion and navigational techniques involving guidewires or flow-directed devices may be used to access the site with any of the catheters described herein. The mechanism will be such as to be capable of being advanced entirely through the catheter to place implantable device at the target site but yet with a sufficient portion of the distal end of the delivery mechanism protruding from the distal end of the catheter to enable detachment of the implantable device. For use in peripheral or neural surgeries, the delivery mechanism will normally about 100-200 cm in length, more normally 130-180 cm in length. The diameter of the delivery mechanism is usually in the range of 0.25 to about 0.90 mm. Briefly, the liquid embolics and/or occlusive devices described herein are typically loaded into a carrier for introduction into the delivery catheter and introduced to the chosen site using the procedure outlined below. This procedure may be used in treating a variety of maladies. For instance, in treatment of an aneurysm, the aneurysm itself may be filled with the embolics (e.g., mechanical devices and/or liquid embolics and bioactive materials) which cause formation of an emboli and, at some later time, is at least partially replaced by neovascularized collagenous material formed around the implanted devices.

A selected site is reached through the vascular system using a collection of specifically chosen catheters and/or guide wires. It is clear that should the site be in a remote site, e.g., in the brain, methods of reaching this site are somewhat limited. One widely accepted procedure is found in U.S. Pat. No. 4,994,069 to Ritchart, et al. It utilizes a fine endovascular catheter such as is found in U.S. Pat. No. 4,739,768, to Engelson. First of all, a large catheter is introduced through an entry site in the vasculature. Typically, this would be through a femoral artery in the groin. Other entry sites sometimes chosen are found in the neck and are in general well known by physicians who practice this type of medicine. Once the introducer is in place, a guiding catheter is then used to provide a safe passageway from the entry site to a region near the site to be treated. For instance, in treating a site in the human brain, a guiding catheter would be chosen which would extend from the entry site at the femoral artery, up through the large arteries extending to the heart, around the heart through the aortic arch, and downstream through one of the arteries extending from the upper side of the aorta. A guidewire and neurovascular catheter as described herein are then placed through the guiding catheter. Once the distal end of the catheter is positioned at the site, often by locating its distal end through the use of radiopaque marker material and fluoroscopy, the catheter is cleared. For instance, if a guidewire has been used to position the catheter, it is withdrawn from the catheter and then the assembly, for example including the liquid embolic and/or implantable device at the distal end, is advanced through the catheter.

The embolic(s) and/or other materials is (are) advanced past the distal end of the catheter and positioned or extruded precisely at the desired treatment site. They are held in place by gravity, shape, size, volume or combinations thereof. Furthermore, the order in which the components (e.g., photopolymerizable material; vaso-occlusive member; retention device; and/or other bioactive materials) are released from the catheter is not critical to the practice of the invention and can be determined by the operator.

Modifications of the procedure and device described above, and the methods of using them in keeping with this invention will be apparent to those having skill in this mechanical and surgical art. These variations are intended to be within the scope of the claims that follow.

What is claimed is:

1. A single-lumen catheter comprising at least one source of electro-magnetic radiation comprising one or more light-transmitting fluids disposed in the wall of the catheter and wherein the light-transmitting fluid is operably linked to an external source of electro-magnetic radiation.

2. The catheter of claim 1, wherein the at least one source of electro-magnetic radiation is disposed at the distal end of the catheter.

3. The catheter of claim 1, wherein the electro-magnetic radiation is ultraviolet light.

4. The catheter of claim 1, wherein at least two electro-magnetic radiation transmission devices are disposed in multiple sides of the catheter.

5. The catheter of claim 1, in combination with a source of photopolymerizable material.

6. The catheter of claim 5, wherein the photopolymerizable material is suitable for deposition at a target site and wherein electro-magnetic radiation emitted from the source of electro-magnetic radiation disposed in the wall of the catheter polymerizes the photopolymerizable material as it is extruded from the catheter.

7. The catheter of claim 5, wherein the photopolymerizable material is selected from the group consisting of polyethyleneglycol diacrylate; poly(ethylene glycol) central block molecules, extended with hydrolyzable oligomers and terminated with acrylate groups; and polyethylene glycol tetraacrylate.

8. The catheter of claim 7, wherein the hydrolyzable oligomers are selected from the group consisting of such as oligo(d,l-lactic acid) and oligo(glycolic acid).

9. The catheter of claim 7, wherein the polymerization of polyethylene glycol tetraacrylate is initiated with triethanolamine, N-vinylpyrollidone, and eosin Y.

10. An assembly for use in depositing material in a vessel comprising
    (a) a catheter according to claim 1;
    (b) a photopolymerizable material; and
    (c) a source of electro-magnetic radiation.

11. The assembly of claim 10, wherein the source of electro-magnetic radiation is disposed within the wall of the catheter at the distal end of the assembly.

12. The assembly of claim 10, wherein the source of electro-magnetic radiation comprises at least one electro-magnetic radiation transmission device disposed within the wall of the catheter and operably linked to an external source of electro-magnetic radiation.

13. The assembly of claim 12, wherein the electro-magnetic radiation transmitting device comprises one or more fiber optic cables.

14. The assembly of claim 12, wherein the electro-magnetic radiation transmitting device comprises one or more light-transmitting fluids.

15. The assembly of claim 12, wherein the electro-magnetic radiation transmitting device comprises one or more light-transmitting wires.

16. The assembly of claim 10, wherein the electro-magnetic radiation is ultraviolet light.

17. The assembly of claim 9, further comprising at least one additional bioactive material.

18. A method of occluding an aneurysm comprising administering to a subject in need thereof a photopolymerizable material using the catheter according to claim 1.

19. The method of claim 18, further comprising administering at least one vaso-occlusive device to the subject through the lumen of the catheter.

20. The method of claim 18, further comprising administering at least one bioactive material to the subject through the lumen of the catheter.

* * * * *